(12) United States Patent
Woodroof et al.

(10) Patent No.: US 9,439,808 B2
(45) Date of Patent: *Sep. 13, 2016

(54) SKIN SUBSTITUTE AND WOUND DRESSING WITH ADDED ANTI-SCAR COMPOUND

(71) Applicants: Permeaderm, Inc. a California Corporation, Carlsbad, CA (US); Univ. of Rochester, Rochester, NY (US)

(72) Inventors: E. Aubrey Woodroof, Carlsbad, CA (US); Richard R. Phipps, Rochester, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/696,433

(22) Filed: Apr. 25, 2015

(65) Prior Publication Data

US 2015/0223989 A1    Aug. 13, 2015

Related U.S. Application Data

(63) Continuation-in-part of application No. 13/897,430, filed on May 19, 2013, now Pat. No. 9,017,405.

(51) Int. Cl.
| | |
|---|---|
| *A61F 2/10* | (2006.01) |
| *A61F 13/00* | (2006.01) |
| *A61L 15/44* | (2006.01) |
| *A61L 15/42* | (2006.01) |
| *A61L 15/18* | (2006.01) |
| *A61L 15/26* | (2006.01) |
| *A61L 27/60* | (2006.01) |
| *A61L 26/00* | (2006.01) |
| *D04B 1/16* | (2006.01) |
| *D04B 1/10* | (2006.01) |
| *C08L 83/04* | (2006.01) |

(52) U.S. Cl.
CPC ... *A61F 13/00063* (2013.01); *A61F 13/00008* (2013.01); *A61F 13/00017* (2013.01); *A61F 13/00029* (2013.01); *A61F 13/00034* (2013.01); *A61L 15/18* (2013.01); *A61L 15/26* (2013.01); *A61L 15/425* (2013.01); *A61L 15/44* (2013.01); *A61L 26/0019* (2013.01); *A61L 26/0066* (2013.01); *A61L 26/0085* (2013.01); *A61L 27/60* (2013.01); *D04B 1/104* (2013.01); *D04B 1/16* (2013.01); *A61L 2300/30* (2013.01); *A61L 2300/406* (2013.01); *C08L 83/04* (2013.01); *D10B 2403/0112* (2013.01); *D10B 2509/022* (2013.01)

(58) Field of Classification Search
USPC ............ 623/1.41, 15.11–15.12, 23.72–23.76, 623/926; 424/443, 447; 435/396–408; 602/42–47
See application file for complete search history.

*Primary Examiner* — Yashita Sharma
(74) *Attorney, Agent, or Firm* — Steven W. Webb

(57) ABSTRACT

An improved skin substitute is presented comprised of a silicone layer backed up with a woven nylon fabric layer, the silicone layer possessing a regular pattern of slits that permit the porosity of the skin substitute to be adjusted by clinicians by means of applying tension to the skin substitute that differentially opens the slits. A variety of therapeutic substances can be applied to the skin substitute to promote healing, including aloe and other medicinal preparations. A layer of water soluble or water insoluble anti-scar compound is also present, the preferred compound being salinomycin.

5 Claims, 2 Drawing Sheets

Knit Structure Terminology

*Courses* are the horizontal rows of loops, while *wales* are the vertical columns of loops in the knit fabric.

SKIN SUBSTITUTE AND WOUND DRESSING WITH ADDED ANTI-SCAR COMPOUND

RELATED APPLICATIONS

This application is a Continuation-In-Part of U.S. patent application Ser. No. 13/897,430 filed 19 May 2013.

FIELD OF THE INVENTION

This invention relates to dressings and bandages for acute and chronic wounds.

BACKGROUND OF THE INVENTION

Wound management involves removal of all non-viable tissue at the wound site, preserving the remaining viable tissue, and providing a moist but not wet environment. An example of successful burn wound dressing is Biobrane, granted U.S. Pat. No. 4,725,279. In 1979 Biobrane was initially studied by American Burn Surgeons; it is still popular world-wide.

In 2007 new art was introduced by this inventor with AWBAT and then with AWBAT Plus, granted U.S. Pat. No. 7,815,931 and covered by several copending patent applications. The key to the success of these products was better porosity in the dressing.

Recently, this inventor has revisited the art of dressing design. The present invention allows passage of fluid adjacent to the wound through the primary dressing into a secondary absorbent dressing as well as improving the kinetics of uninterrupted wound healing. Technology of this dressing has evolved into a new product which possesses all the characteristics and attributes known to be important for optimal wound healing, as well as containing certain advances that result in minimization of wound desiccation and infection complication.

SUMMARY OF THE INVENTION

Wound sites have variable amounts of exudate/transudate/plasma present, from dry to weepy. The clinician must cleanly debride the wound, close it and manage wound healing in a moist but not wet environment to achieve optimal results in both acute and chronic wounds.

The present invention provides a dressing that possesses all the properties and attributes of an ideal skin substitute and, in addition, has 'variable porosity' controlled by the clinician from essentially zero porosity to what the wound requires. The present invention enables the clinician to move the fluid exuding from the wound through the primary dressing into an absorbent secondary dressing without disturbing the kinetics of healing or causing pain to the patient.

The present invention is cost effective at every level. Patients get their wounds managed with minimal pain and optimal healing times. The dressing is cost effective as the hospital needs to inventory only one primary dressing for acute wounds (burns) and one for chronic wounds; each has a two year shelf-life at room temperature.

The present invention is composed of one or two biological layers sprayed on in one or two separate operations. The first layer sprayed onto the nylon side of the "variable porosity" silicone membrane will be: (1) a solution of pure Aloe (Aloesin, Immuno10, Qmatrix and Loesyn—each hydrophilic and hygroscopic); (2) a solution of pure Aloe and hypoallergenic USP Pharmaceutical Grade porcine gelatin; or (3) a fine suspension of pure Aloe, gelatin and ECM (as fine insoluble particles or hollow spheres in water—the latter possesses improved healing properties). In vitro, the Aloe component has been demonstrated to cause a variety of cells to attach and proliferate; as well as increase synthesis of collagen and alpha smooth muscle actin. ECM may be added to the biologicals described above and is a mixture from human fibroblasts that is known to cause rapid cell proliferation and tissue growth. Previous wound dressings and skin substitutes, as taught in U.S. Pat. No. 7,815,931 contain gelatin, a pure Aloe component, chondroitin 4 & 6 sulfate, and vitamin C & E. In contrast the current dressing will have two layers of biologicals applied in separate spraying operations as described above.

The first coat will contact the wound after the second coat of hypoallergenic bovine spongiform encephalopathy (BSE)-free United States Pharmaceutical (USP)-grade gelatin interacts with fibrin in the wound to achieve early adherence. The second coat of biologicals stimulates the healing process during the interval where the dressing invention is in contact with the wound and is stable requiring 100 degree water for 30 minutes to remove from the "variable porosity" silicone/nylon surface.

Water soluble or water insoluble anti-scar compound(s) can be incorporated into the 3D matrix of this variable porosity skin substitute. The preferred embodiment of the anti-scar compound is salinomycin, which can be incorporated in two ways—into the hydrophobic solid silicone component of the skin substitute or into the water soluble biological coating used to coat the 3D surface.

DETAILED DESCRIPTION

The present invention is similar in composition to earlier skin substitutes in that they each have a thin silicone component, the silicone membrane selected in a thickness from 0.001" to 0.005", and an underlying thin knitted nylon component. The present invention differs from its ancestors in that it has "variable porosity" controlled by the clinician; the pore size in the thin silicone will be essentially zero (with no stretch, in relaxed mode) to a higher porosity (proportional to the stretch applied). See FIG. 1 for the optional stretch modes. In addition, the present invention differs in the composition of biological coatings applied to both components and how these coatings interact with the wound over time.

The pores of prior art skin substitutes/dressings are of a fixed size (Biobrane 1.2%; AWBAT and AWBAT Plus 5.5% and 7.5%) in the unstretched open position; the silicone is cured while the skin substitute pores are open. Once cured the pores cannot close or be reduced in size; this causes wound desiccation and punctate scarring. As in FIG. 1, in contrast, the openings are made after the silicone component has been cured, and are in the shape of slits, not holes. The figure shows the skin substitute silicone layer up with the slits exposed.

Figure 1:
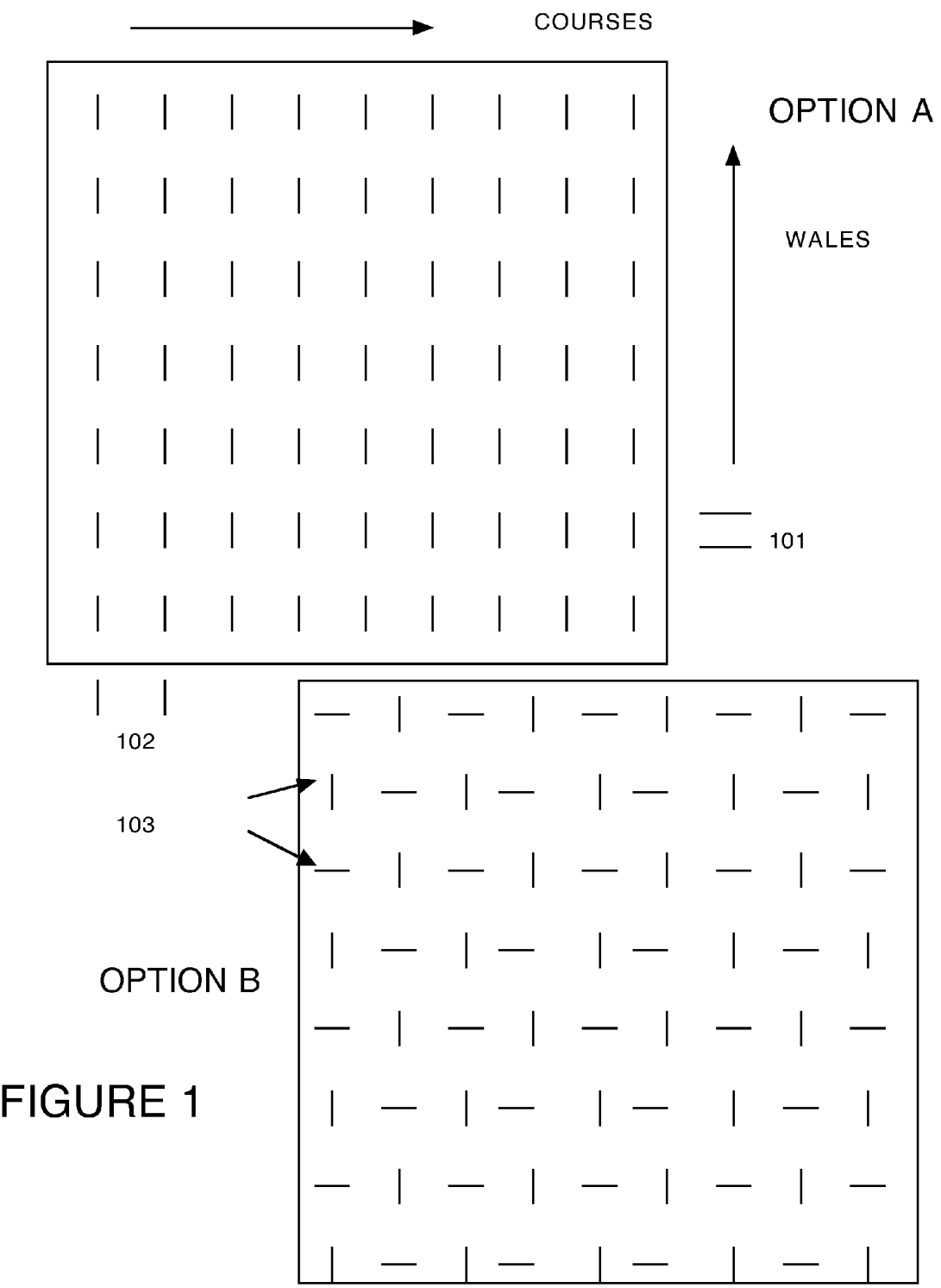
FIG. 1. The embodiments of the invention, showing the slit openings
Figure 2:
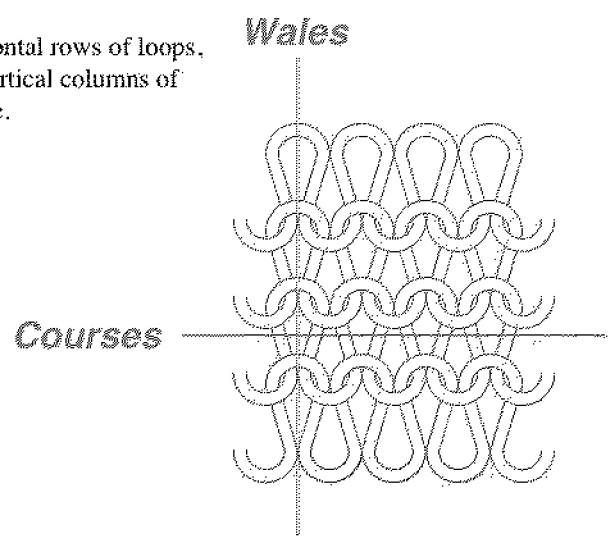
FIG. 2. The wale and course nature of the woven fabric

The "wale" and "course" orientations of stitching of the knitted nylon component of the invention are shown in FIG. 2. The preferred embodiment of the invention is shown in FIG. 1. In this embodiment, designed for burns, the slits 103 made in the silicone are approximately 0.250" long 101 with a space of 0.250" between slits 102; parallel rows of slits are 0.250" apart. The parallel rows of slits are oriented such that the slits are parallel to the "wale" orientation of the Jersey stitch pattern of the knitted nylon component. The "wale" orientation has measurably less elongation than the "course" orientation.

Because of the orientation of the slits, stretch along the axis of the slits is minimal and stretch perpendicular to the slit axes is maximized. With no stretch of the silicone/nylon membrane the slits cannot be seen without magnification while observing from above and provide essentially zero porosity.

The preferred embodiment is effective, particularly on partial thickness burns where punctate scarring has been observed. In the preferred embodiment, with no stretch, the wound is protected by an essentially continuous thin silicone membrane which minimizes wound desiccation and punctate scarring. This enables the clinician to stretch the dressing parallel to the direction of the slits with minimal opening of the slits. This is parallel to the "wale" direction of the underlying fabric. Fluids from the wound can still escape through the closed slits and be absorbed into a secondary dressing, which can be removed and replaced without interfering with the healing process or causing pain to the patient.

Figure 3:
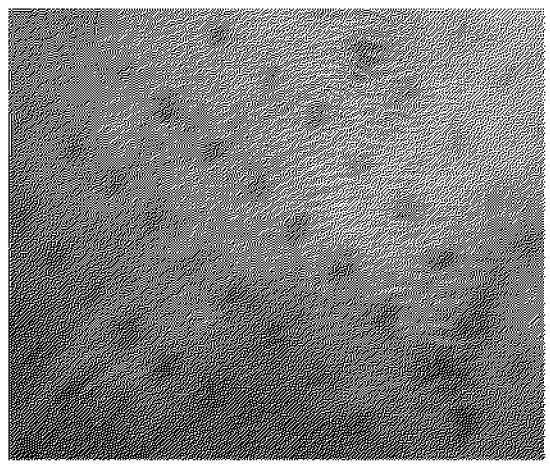
FIG. 3. An example of punctuate scarring

The combination of a primary dressing that requires minimal changes and a secondary dressing that is easy to change and replace reduces wound maintenance costs which benefits patient, staff and hospital. An example of punctate scarring is illustrated in FIG. 3; the figure shows the skin of a patient whose burn was covered with the ancestor AWBAT dressing with a fixed porosity of at least 5.5%.

Chronic, slow healing wounds require similar treatment as burns in that all necrotic tissue must be removed before closing the wound with a primary dressing. In the chronic wound, exudate and other fluids are often removed with negative pressure wound therapy (NPWT). A negative pressure above the wound or a positive pressure from the wound causes exudate and other wound fluids to pass through the primary dressing into a secondary dressing. The primary dressings currently used during NPWT are: urethane foam, polyvinyl alcohol foam or cotton gauze; all require frequent dressing changes and infection complications have been reported when these dressings are not changed frequently.

The present invention will have two layers of water-soluble biologicals; first a clotting outer layer containing hypoallergenic BSE free USP Pharmaceutical grade gelatin. This layer contacts the wound first and stimulates initial adherence of the dressing to the cleanly debrided wound. The second layer of pure Aloe or Aloesin, pure Aloe and BSE free gelatin, or a mixture of pure Aloe, BSE free gelatin and ECM interact with the wound to stimulate the rate of healing while adherent to the wound. The first layer is deposited directly on the nylon side of the "variable porosity" silicone/nylon surface and is stable, i.e. requires 100 degree water for 30 minutes to remove from the "variable porosity" silicone/nylon surface.

Water soluble or water insoluble anti-scar compound(s) can be incorporated into the 3D matrix of this variable porosity skin substitute. The preferred embodiment of the anti-scar compound is salinomycin, which can be incorporated in two ways—into the hydrophobic solid silicone component of the skin substitute or into the water soluble biological coating used to coat the 3D surface. The structure of salinomycin is shown below.

In one embodiment, salinomycin is formulated in a topical composition comprising salinomycin and a carrier or excipient suitable for dermal application. The term "carrier or excipient" as used herein, refers to a carrier or excipient that is conventionally used in the art to facilitate the storage, administration, and/or the biological activity of an active compound. A carrier may also reduce any undesirable side effects of the active compound. A suitable carrier is, for example, stable, e.g., incapable of reacting with other ingredients in the formulation. In one example, the carrier does not produce significant local or systemic adverse effect in recipients at the dosages and concentrations employed for treatment. Such carriers and excipients are generally known in the art. Suitable carriers for this invention include those conventionally used, e.g., water, saline, aqueous dextrose, and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Suitable carriers for topical application of a compound are known in the art and include, for example, methyl cellulose (e.g., 3% methylcellulose; Beck et al., Growth Factors, 3: 267, 1990), silver sulfadiazene cream (Schultz et al., Science, 235: 350, 1985), multilamellar lecithin liposomes (Brown et al., Ann Surg., 208: 788, 1988) or hyaluronic acid (Curtsinger et al., Surg. Gynecol. Obstet., 168: 517, 1989). In some examples, the carrier can be a co-polymer, a paste or a hydrogel.

In some embodiments, the topical composition as described herein according to any embodiment additionally comprises a compound that enhances or facilitates uptake of salinomycin into and/or through skin of a subject. Suitable dermal permeation enhancers are, for example, a lipid disrupting agent (LDA), a solubility enhancer, or a surfactant.

This is the preferred embodiment of the invention. The technology to create this invention is listed as the preferred embodiment of this invention, but other methods are possible and are within the contemplation of this patent.

What is claimed is:

1. A skin substitute, the skin substitute comprised of two layers of material,
   the first layer of material, an upper layer, comprised of a silicone membrane, the second layer, a lower layer, comprised of a woven nylon fabric,
   the silicone membrane selected in a thickness from 0.001" to 0.005",
   the upper layer possessing a plurality of slits in its surface, said slits made after the two layers are joined together, said slits in a pattern comprised of multiple rows of parallel slits,
   the lower layer woven in a regular pattern with a perpendicular wale and course orientation, the slits on the surface either following the wale direction of the lower layer or crossing the wale direction of the lower layer perpendicularly, said upper layer and said lower layer treated with a plurality of layers of medicinal or therapeutic substances applied to the two layers of the skin substitute, said lower layer also treated with a water soluble or water insoluble anti-scar compound, said slits placed in said upper layer such that the skin substitute has essentially zero porosity with no stretching tension placed on it, the porosity of said skin substitute variable proportional to the amount of stretching tension and the direction in which said stretching tension is placed on the skin substitute, the direction of stretching tension dependent on the orientation of said slits with the wale and course orientation of the woven nylon fabric, the skin substitute designed to place the woven nylon fabric side down on top of a wound when in use, the skin substitute selected to be used in combination with an absorptive dressing placed above said skin substitute over the wound.

2. The skin substitute of claim 1 where the plurality of slits are oriented in parallel with the wale orientation of the lower layer.

3. The skin substitute of claim 2 where the plurality of layers of medicinal and therapeutic substances are selected from the list of hypoallergenic BSE free USP Pharmaceutical grade gelatin, pure aloe, aloesin, ECM.

4. The skin substitute of claim 1 where the anti-scar compound is comprised of salinomycin.

5. The skin substitute of claim 4, wherein salinomycin is incorporated into (1) the silicone membrane of the skin substitute or (2) the plurality of layers of medicinal or therapeutic substances.

* * * * *

UNITED STATES PATENT AND TRADEMARK OFFICE
CERTIFICATE OF CORRECTION

Page 1 of 1

PATENT NO. : 9,439,808 B2
APPLICATION NO. : 14/696433
DATED : September 13, 2016
INVENTOR(S) : E. Aubrey Woodroof and Richard P. Phipps It is certified that error appears in the above-identified patent and that said Letters Patent is hereby corrected as shown below:

On the Title Page

Item (72):
Substitute Richard P. Phipps for Richard R. Phipps as the second inventor on the above patent.

Signed and Sealed this
First Day of August, 2017

Joseph Matal
*Performing the Functions and Duties of the*
*Under Secretary of Commerce for Intellectual Property and*
*Director of the United States Patent and Trademark Office*